United States Patent
Bauman et al.

(10) Patent No.: US 6,288,114 B1
(45) Date of Patent: Sep. 11, 2001

(54) METHOD OF ALTERING NUTRITIONAL COMPONENTS OF MILK PRODUCED BY A LACTATING ANIMAL

(75) Inventors: Dale E. Bauman, Ithaca, NY (US); Mark A. McGuire, Moscow, ID (US); Mikko Griinari, Helsinki (FI); P. Yvan Chouinard, Quebec (CA)

(73) Assignee: Cornell Research Foundation, Inc., Ithaca, NY (US)

(*) Notice: Subject to any disclaimer, the term of this patent is extended or adjusted under 35 U.S.C. 154(b) by 0 days.

(21) Appl. No.: 09/103,366

(22) Filed: Jun. 23, 1998

Related U.S. Application Data (60) Provisional application No. 60/050,539, filed on Jun. 23, 1997.

(51) Int. Cl.$^7$ .................................................. A61K 31/202
(52) U.S. Cl. .............................................. 514/547; 424/535
(58) Field of Search ........................ 514/547; 424/535; 435/134

(56) References Cited

U.S. PATENT DOCUMENTS

| | | | |
|---|---|---|---|
| 3,925,560 | 12/1975 | Scott et al. ................................. | 426/2 |
| 4,216,234 | 8/1980 | Rawlings et al. ......................... | 426/2 |
| 5,416,115 * | 5/1995 | Erdman et al. ....................... | 514/560 |
| 5,503,112 | 4/1996 | Luhman et al. ....................... | 119/174 |
| 5,670,191 * | 9/1997 | Cummings et al. ...................... | 426/2 |
| 5,770,247 | 6/1998 | Satter et al. ............................. | 426/2 |

OTHER PUBLICATIONS

Kalscheur, K.F. et al., J. Dairy Sci., vol. 80(9), p. 2115–2126, Sep. 1997.*
Schoedre, J.W. et al., "Using a Total Mixed Ration for Dairy Cows," North Dakota State Univ., NDSU Extension Service, AS–769 (Revised). Downloaded from the Internet, Oct. 1997.*
Netrition—Conjugated Linoleic Acid (CLA). Downloaded from the Internet, 1997.*
CLA 60 caps 500 mg. Downloaded from the Internet.*
Casper, D.P. et al., J. Dairy Sci., vol. 71, p. 1267–1274, 1988.*
Jahreis, G. et al., Nutrition Research, vol. 17(9), p. 1479–1484, 1997.*
Storry, J.E. et al., Brit. J. Nutr., vol. 19, p. 101–109, 1965.*
Jahreis, G. et al., Fett/Lipid, vol. 98(11), p. 356–359, 1996.*
Griinari, J.M. et al., J. Dairy Sci., vol. 79(Supp. 1), p. 177, abstract #P189, 1996.*
Astrup, H. N., L. Vik–Mo, A. Ekern, and F. Bakke. 1976. Feeding protected and unprotected oils to dairy cows. J. Dairy Sci. 59:426–430.
Banks, W., J. L. Clapperton, A. K. Girdler, and W. Steele. 1984. Effect of inclusion of different forms of dietary fatty acid on the yield and composition of cow's milk. J. Dairy Res. 51:387–395.

Chin, S. F., J. M. Storkson, K. J. Albright, M. E. Cook and M. W. Pariza. 1994, Conjugated linoleic acid is a growth factor for rats as shown by enhanced weight gain and improved feed efficiency. J. Nutr. 124:2344–2349.
Davis, C. L., and R. E. Brown. 1970. Low–fat milk syndrome. p.545–565 in Digestion and Metabolism in the Ruminant. A. T. Phillipson, ed. Oriel Press, Newcastle upon Tyne, England.
Erdman, R. 1996. Milk fat depression: some new insights. Proceedings, Tri–State Dairy Nutrition Conference, Fort Wayne, IN, pp. 1–16. May.
Gaynor, P. J., R. A. Erdman, B.B. Teter, J. Sampugna, A. V. Capuco, D. R. Waldo, and M. Harnosh. 1994. Milk fat yield and composition during abomasal infusion of cis or trans octadecenoates in Holstein Cows. J. Dairy Sci. 77:157–165.
Griinari, J. M., P.Y. Chouinard, and D. E. Bauman. 1997. Trans fatty acid hypothesis of milk fat depression revised. p. 208–216 in Cornell Nutr. Conf Feed Manuf, Rochester, NY. Cornell Univ., Ithaca, NY.
Griinari, I M., D. A. Dwyer, M. A. McGuire, D. E. Bauman, D. L. Palmquist, and K. V. V. Nurmela. 1998. Trans–octadecenoic acids and milk fat depression in lactating dairy cows. J Dairy Sci. 81:1251–1261.
Kalscheur, K. F., B. B. Teter, L. S. Piperova, and R. A. Erdman. 1997. Effect of dietary forage concentration and buffer addition on duodenal flow of trans–CI&I fatty acids and milk fat production in dairy cows. J Dairy Sci. 80:2104–2114.
Newbold, J.R., K.L. Robertshaw and H.W. Morris. 1998. Associates between concentration of fat and intermediates of ruminal biohydrogenation in milk of dairy cows. 10 Proc. Brit. Soc. Anim. Sci., pp. 224. (abstract).

(List continued on next page.)

Primary Examiner—Jean C. Witz
(74) Attorney, Agent, or Firm—Brown & Michaels, PC (57) ABSTRACT

The present invention alters mammary synthesis of fat to improve milk quality. These changes in milk composition represent improvements in nutritional quality consistent with contemporary dietary recommendations. Of special importance is the disclosure of new data relating to specific conjugated linoleic acids (CLA), potent naturally occurring anti-carcinogens. In the course of an investigation to enhance milk content of conjugated linoleic acid, it was discovered that abomasal infusion of a single TFA isomer caused a marked milk fat depression. This observation was unexpected because the prior art has consistently shown that body fat and milk fat always show reciprocal changes in lactating cows and indicated that CLA's generally reduced body fat in growing animals. The current disclosure demonstrates that an increase in milk fat content of a specific TFA isomer, trans-10 $C_{18:1}$. (Griinari et al., 1997, 1998) causes MFD. This observation is in conflict with the prior art that taught that an increase in total TFA caused MFD. These results are applicable to other domestic lactating mammals (e.g., pigs). Upon the infusion of CLA, a portion of the CLA is transferred to the mammary gland and incorporated into milk fat. Hence, the methods disclosed increase the levels of CLA found in milk, thereby improving the nutritional benefits to human health associated with CLA.

12 Claims, 5 Drawing Sheets

OTHER PUBLICATIONS

Pennington, I A., and C. L. Davis. 1975. Effects of intraruminal and intra-abomasal additions of cod liver oil on milk fat production in the cow. J Dairy Sci. 58:49–55.

Romo, G., D. Casper, R. Erdman, and B. B. Teter. 1996. Abomasal infusion of cis and trans fatty acid isomers and energy metabolism of lactating dairy cows. J Dairy Sci. 79:2005–2015.

Selner, D. R., and L. H. Schultz. 1980. Effects of feeding oleic acid or hydrogenated vegetable oils to lactating cows. J Dairy Sci. 63:1235–1241.

Teter, B.T., I Sampugna and M. Keeney. 1990. Milk fat depressionin C57BI/6j mice consuming partially hydrogenated fat. J Nutr. 120:818–814, #8 Aug..

Wonsil, B. J., I H. Herbein, and B. A. Watkins. 1994. Dietary and rurninally derived trans–18:1 fatty acids alter bovine milk lipids. J Nutr. 124:556–565.

* cited by examiner

METHOD OF ALTERING NUTRITIONAL COMPONENTS OF MILK PRODUCED BY A LACTATING ANIMAL

REFERENCE TO RELATED APPLICATIONS

This application claims an invention which was disclosed in Provisional Application No. 60/050,539, filed Jun. 23, 1997, entitled "METHOD OF ALTERING NUTRITIONAL COMPONENTS OF MILK PRODUCED BY A LACTATING ANIMAL". The benefit under 35 USC §119(e) of the United States provisional application is hereby claimed, and the aforementioned application is hereby incorporated herein by reference.

FIELD OF THE INVENTION

The invention pertains to the field of methods of altering fat and fat composition of milk produced by a lactating animal. More particularly, the inventions pertain to methods of decreasing the milk fat content of milk and increasing the percentage of conjugated linoleic acid isomers in milk.

BACKGROUND OF THE INVENTION

Today, consumers are much more aware of nutrition, particularly dietary fat. This awareness includes a shift toward consumption of low fat products, including low fat milk products. Thus, there is interest in reducing the fat percentage of milk produced by the cow. Milk fat is composed mainly of triglycerides. The mammary cell absorbs the precursors or building blocks for milk production (e.g. the component fatty acids of milk: acetate, B-hydroxybutyrate, and preformed fatty acids) from the circulation. Several reviews have summarized the factors that affect milk fat percentage and yield. Nutrition plays a major role, and certain nutritional practices cause milk fat depression by mechanisms that have not been clearly established.

The milk fat depression (MFD) which occurs when "high concentrate diets" or diets primarily composed of one type nutrient, in this case grains, are fed represent an extreme situation where the rate of milk fat synthesis in an individual cow can decrease by 50% or more. In addition, several other dietary manipulations including rumen active fats, small particle size forage, lush pasture and ionophores all result to varying degrees in decreased milk fat yield. These nutritional situations involve changes in rumen fermentation or metabolism, which are believed to directly or indirectly result in a shortage of lipid precursors at the mammary gland. The actual mechanisms involved in MFD had not been fully explained but several theories have been proposed. These theories can be broadly summarized into two categories: (1) theories which consider the depression to be an indirect consequence of a shortage in the supply of lipid precursors to the mammary gland and (2) those that attribute MFD to a direct inhibition of mammary gland synthesis of milk fat.

The most widely held theory is the glucogenic-insulin theory of milk fat depression. This theory explains the mammary gland shortage of milk fat precursors based on the concept that organs and tissues compete for nutrients. In this competition the uptake of lipogenic precursors by adipose tissue, but not the mammary gland, is responsive to changes in circulating concentrations of insulin. The glucogenic-insulin theory proposes that increased insulin release, which occurs with certain diets (e.g., diets with a large proportion of grains), preferentially channels nutrients to adipose tissue resulting in a shortage at the mammary gland and, thus, milk fat depression.

Other theories suggest that milk fat depression is caused by a direct inhibition at the mammary gland of one or more steps in the synthesis of milk fat. A number of compounds that could be derived from the diet or produced by ruminal fermentation or animal metabolism have been suggested as possible factors that could inhibit milk fat synthesis in the mammary gland. These include trans-octadecenoic acids, methylmalonic acid and cyclopropene fatty acids such as sterculic acid. Direct inhibition of milk fat synthesis by trans-octadecenoic acids (frequently referred to as trans fatty acids; TFA) was first proposed more than two decades ago (Davis and Brown, 1970). Pennington and Davis (1975) further speculated that TFA, resulting from the partial hydrogenation of unsaturated fatty acids in the rumen, were involved in causing MFD with high concentrate diets as well as when polyunsaturated oils were fed. Subsequent studies with cows, goats and mice have demonstrated that TFA produced in the rumen or added to the diet were associated with depressed milk fat production (Astrup et al. 1976; Selner and Schultz, 1980; Wonsil et al. 1994; Gaynor et al. 1994; Romo et al. 1996). Many of these studies used partially hydrogenated vegetable oils as the dietary source of trans-fatty acids and authors concluded that MFD was caused by trans-fatty acids.

U.S. Pat. No. 5,416,115 (hereinafter '115 patent) issued to Erdman et al. in 1995 teaches a method of regulating milk fat by administering trans-fatty acids to lactating cows. The '115 patent defines trans-fatty acids as trans-octadecenoic fatty acids (column 1, line 16–20) and the patent claims to be the first to recognize this connection between TFA and MFD. However, the '115 patent fails to quote much of the prior art (e.g. Davis and Brown, 1970; Pennington and Davis, 1975) and misrepresents other work (e.g. Selner and Schultz, 1980). Further, the '115 patent dismisses the prior work by concluding, "none of these studies have established a causative role between the amount and/or type of isomers of fatty acids ingested by cows and resulting milk fat concentrations." This is interesting because the inventors own scientific work (see review by Erdman, 1996) and the '115 patent also fail to postulate or establish a specific causative role between milk fat depression and specific trans isomers in terms of "amount and/or type of isomers of fatty acids."

Figure 1:
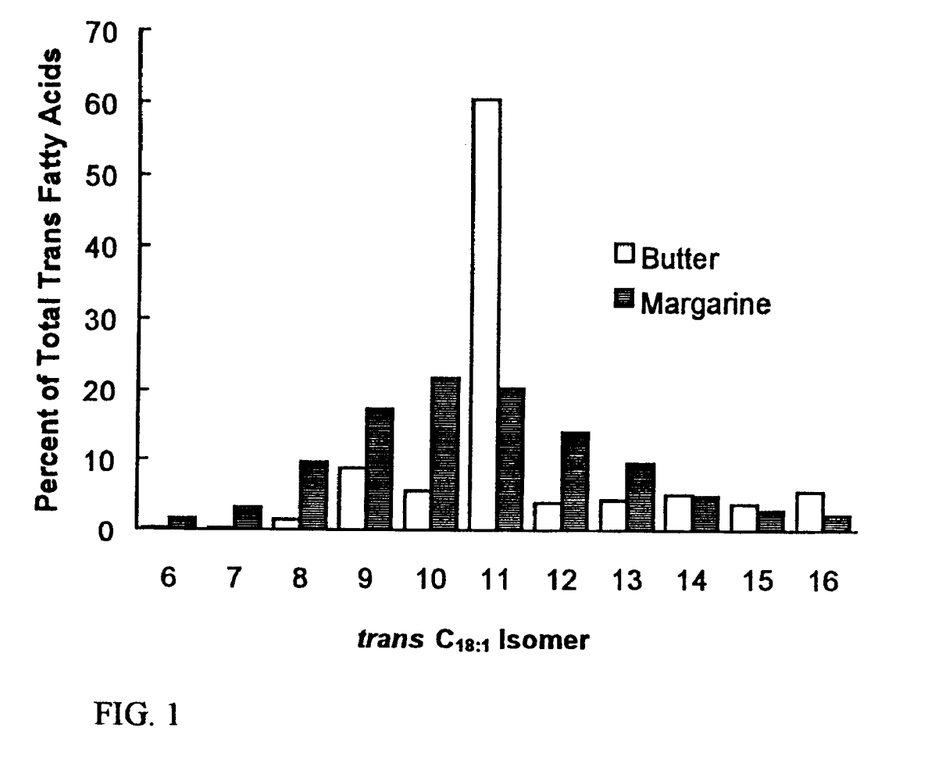
FIG. 1 shows a distribution of trans-octadecenoic fatty acid isomers in butter and margarine.

The '115 patent claims all trans-fatty acid isomer species (column 12 and 13) as the cause of MFD. However, the inventors of that patent make no distinction between specific trans-isomers in their patent or in their scientific publications (e.g. Teeter et al. 1990; Gaynor et al. 1994; Romo et al. 1996; Kalscheur et al. 1997). In fact, their scientific publications emphasize that MFD is related to total trans-fatty acids (see review by Erdman, 1996). Later data clearly shows that some trans-fatty acids do not cause milk fat depression while others are responsible for some MFD. For example, one can increase trans-11 octadecenoic fatty acid content of milk with no change in overall milk fat percentage. This particular fatty acid predominates in milk fat. When compared to partially hydrogenated vegetable fat (e.g. margarine), butter (a product of milk) contains a wider range of trans isomers (see FIG. 1). Initial data shows MFD was correlated with total trans-fatty acid content of milk fat (Erdman 1996; Griinari et al. 1998). However, using more refined techniques the current invention demonstrates that changes in milk fat content are related to changes in specific trans-isomers and not to total TFA isomers (Griinari et al. 1997, 1998). For example, one can increase trans-11 octadecenoic acid content of milk fat with, no change in overall milk fat percentage. Thus, the broad guesses in the '115 patent about the general nature of trans-fatty acids are just guesses. The patent fails to provide sufficient guidance or enablement to those skilled in the art to determine which compounds cause milk fat depression.

SUMMARY OF THE INVENTION

Briefly stated, the present invention alters mammary synthesis of fat to improve milk quality. These changes in milk composition represent improvements in nutritional quality consistent with contemporary dietary recommendations. Of special importance is the disclosure of new data relating to specific conjugated linoleic acids (CLA), potent naturally occurring anti-carcinogens. In the course of an investigation to enhance milk content of conjugated linoleic acid, it was discovered that abomasal infusion of a CLA preparation caused a marked milk fat depression.

This observation was unexpected as prior work had indicated that CLA's generally reduced body fat in growing animals. A reduction in milk fat upon abomasal infusion of a CLA preparation was surprising because the prior art had consistently shown that body fat and milk fat always show reciprocal changes in lactating cows. In addition, prior studies observed a wide variation in CLA content of milk from cows during lactation but no one had reported a relationship with fat content of milk. The current disclosure demonstrates that an increase in milk fat content of a specific TFA isomer, trans-10 $C_{18:1}$. (Griinari et al., 1997, 1998) causes MFD. This observation is in conflict with the prior art that taught that an increase in total TFA caused MFD. These results are applicable to other domestic lactating mammals (e.g. pigs, sheep).

The milk fat depression observed with CLA infusion was also unexpected based on conflicting results with lactating laboratory animals. Just as occurs in cows, addition of TFA to the diet of lactating mice caused a depression in milk fat content so that milk energy secretion and the growth of the nursing pups was markedly decreased (Teter et al. 1990). In contrast, when CLA was added to diet of lactating rats, lactational performance was improved so that growth of the nursing pups was increased (Chin et al. 1994).

Upon the infusion of CLA a portion of the CLA is transferred to the mammary gland and incorporated into milk fat. Hence, the methods of the present invention increase the concentration of CLA, with consequent benefits to human health associated.

According to an embodiment of the invention, a method of altering the concentration of milk fat in milk produced by a lactating mammal includes administering to the lactating mammal an effective amount of a conjugated linoleic acid compound sufficient to decrease the fat content of milk produced by the lactating mammal and increase the milk content of conjugated linoleic acid isomers such that the conjugated linoleic acid compound is capable of bypassing initial digestive processes or rumen bacterial fermentation.

According to an embodiment of the invention a method of elevating the level of trans-fatty acid 10 C18:1 in the milk of a lactating ruminant includes administering to the lactating ruminant an amount of a conjugated linoleic acid compound effective to decrease the fat content of milk produced by the lactating mammal and increase the milk content of conjugated linoleic acid isomers such that the conjugated linoleic acid compound is not modified in the rumen of the lactating ruminant.

According to an embodiment of the invention, a method of altering the concentration of milk fat in milk produced by a lactating ruminant includes administering to the lactating ruminant an amount of a conjugated linoleic acid compound effective to decrease the fat content of milk produced by the lactating mammal and increase the milk content of conjugated linoleic acid isomers such that the conjugated linoleic acid compound is not modified in the rumen of the lactating ruminant.

DESCRIPTION OF THE PREFERRED EMBODIMENT

Milk and other animal products are important as a food source contributing more than a third of the calories, and between a third and all of the major nutrients in the U.S. food supply. For example, sixteen ounces of milk supplies ⅓ of the daily protein requirement of an adult and this protein provides an almost perfect pattern of amino acids for body needs and absorption. However, animal products also contribute more than half of the total fat and three-fourths of the saturated fatty acids in our diet, food components that may adversely affect an individual's health. Thus, the National Academy of Science has emphasized a need to develop strategies for changing the nutrient content of animal products consistent with contemporary dietary recommendations.

ABBREVIATION KEY

CLA Conjugated linoleic acid
MFD Milk fat depression
TFA Trans fatty acids
SF Saturated fats
UF Unsaturated fats
HF high fiber diet
LF low fiber diet In the case of milk fat, the disclosure of the present invention is significant for several reasons. In a producing dairy cow, about 30% of animals' net energy requirement are needed for maintenance and 70% is used for milk synthesis. About one-half of that used for milk synthesis is required just for the synthesis of the fat component of the milk produced. Thus, a major portion of the producer's expense for feed resources is associated with the energy requirements to make milk fat. Decreasing the fat content of milk would improve feed efficiency in dairy cows and other food animals (e.g. lactating pigs), lower costs, and improve the nutritional characteristics of the produced milk relative to the dietary recommendations of the National Academy of Science. The invention accomplishes these goals while increasing the content of conjugated linoleic acids (CLA) in milk fat. This increase of CLA content gives the milk produced as a result of the method described herein anti-carcinogenic activity as well as other positive health benefits.

A characteristic of the biology of milk fat depression is the reciprocal concurrent changes that occur in body fat content and milk fat content. These reciprocal changes are observed for all the types of MFD, and the concept of decreased milk fat secretion and increased body fat accretion is accommodated in all of the theories of MFD. In the glucogenic-insulin theory, the insulin stimulated increase in body fat stores in adipose tissue is proposed to cause a shortage of lipid precursors for mammary gland synthesis of milk fat. In other theories involving a direct inhibition at the mammary gland of one or more steps in the synthesis of milk fat, the changes in body fat accretion and adipose tissue metabolism are consequences of the more positive energy balance from the reduced output of milk fat.

Conjugated linoleic acid (CLA) isomers are a mixture of positional and geometric isomers of octadecadienoic (linoleic) acid with conjugated double bonds. There are several possible isomers of CLA of which cis-9, trans-11 CLA is the most common in food products from ruminants. CLA is formed by rumen microorganisms as an intermediate in the bio-hydrogenation of dietary unsaturated fatty acids (e.g. the "addition" of $H_2O$ to saturate fatty acids and remove double bonds). The pathway of bio-hydrogenation is shown below:

Linoleic Acid (cis-9, cis-12 $C_{18:2}$)

⇓

CLA (conjugated linoleic acid) (cis-9, trans-11 $C_{18:2}$)

⇓

Trans Fatty Acid (trans-11 $C_{18:1}$)

⇓

Stearic Acid (saturated $C_{18:0}$)

Most of the dietary linoleic acid is fully hydrogenated by rumen bacteria, but detectable levels of CLA are absorbed and incorporated into milk fat. This is done mostly as the cis-9, trans-11 CLA isomer. There is interest in increasing milk fat content of CLA because it is one of the most potent, naturally occurring anti-carcinogens. CLA also has other positive biological effects including effects to alter nutrient partitioning in growing animals (more lean, less body fat), enhanced immune function, prevention of diabetes and inhibition of atherogenesis.

CLA's are unique because they are only found in food derived from animal sources or animal byproducts (e.g. milk) and the concentrations needed to realize anticancer efficacy are expressed at concentrations close to the levels of current human consumption. Typically, the source for the CLA and TFA in milk fat are the result of incomplete bio-hydrogenation of dietary unsaturated fat by rumen bacteria. The present invention teaches that some of the unique CLA and TFA isomers that arise from the incomplete rumen bio-hydrogenation and commercial hydrogenation are the cause of MFD.

A reduction in milk fat synthesis is one strategy to improve the nutritional quality of milk. The present invention discloses a method that allows dairy cows to routinely produce milk with a lower fat content and higher CLA content. To maintain this type of production an understanding of milk fat synthesis is needed. In commercial dairy production, certain practices such as feeding plant oils, high-energy diets, or finely chopped roughage can, under the right conditions, result in MFD. The prevailing theory has been that MFD was caused by an elevation in insulin release. The rising production and release of insulin resulting in nutrients being preferentially channeled to body fat rather than milk fat synthesis. However, the studies disclosed herein demonstrate that this theory of insulin's role in the mechanism of MFD is incorrect.

The present invention shows that MFD is a consequence of the production of a unique fatty acid. These fatty acids are produced from partial bio-hydrogenation of dietary unsaturated fatty acids by rumen bacteria or incomplete commercial hydrogenation. These unique fatty acids are then incorporated into milk fat. During this conversion into milk fat these fatty acids have an inhibitory effects on the synthesis and incorporation of other fatty acids into milk fat triglycerides. This inhibitory effect results in a reduction in total milk fat content. Bio-hydrogenation of unsaturated fatty acids in the rumen typically produces 9-cis, 11-trans $C_{18:2}$ and 11-trans $C_{18:1}$ as intermediate products. The former represents a fatty acid with conjugated double bonds referred to as CLA and the latter represents a trans fatty acid with a single double bond typically referred to as TFA. However, commercial hydrogenation produces other CLA and TFA isomers and the present invention shows these unique isomers are also present when MFD occurs.

There is a wide range of dietary situations which can alter the extent of rumen bio-hydrogenation including concentration level of microbiota in the rumen, intake of lush pasture, dietary particle size, effective fiber level and the feeding of unsaturated fats. Studies have shown that elevated levels of total TFA in milk fat correlate well with MFD. However, as part of the current disclosure TFA isomers were examined in detail, and it was found that MFD is not related to total TFA, but rather to a specific trans isomer, namely trans-10 $C_{18:1}$ (Griinari et al., 1997, 1998). A recent abstract has verified this work (Newbold et al. 1998). The results indicate that even though TFA's are incorporated into milk fat, the unique structure and/or physical characteristics of the specific trans-10 isomer trans-10 $C_{18:1}$ must impair the synthesis and incorporation of other fatty acids into milk fat triglycerides.

The role of CLA in MFD had not been examined until the experiments in the present invention. The present invention teaches that including a CLA isomer mixture in animal diets can routinely reduce the production of milk fat and increase the milk content of CLA. This is significant for many reasons including the fact that a substantial portion of the average cow's net energy requirement is being used to make milk fat; thus, use of the invention would markedly improve feed efficiency. However, another aspect of great importance is the potential for elevating CLA concentration in milk. CLA is a potent anti-carcinogen. Of the limited number of naturally occurring substances that have been demonstrated to have anti-carcinogenic activity in experimental models, all are of plant origin except for CLA. CLA is unique because it is only present in foods from animal sources, and its anticancer efficacy is expressed at concentrations close to normal human consumption levels. Using experimental models, studies have shown that dietary CLA markedly reduces the incidence of a wide range of cancers including breast tumors, and epidermal and stomach carcinomas. Further, dairy products are the major source of CLA in human diets.

EXAMPLE 1

CLA-60 Infusion

Figure 2:
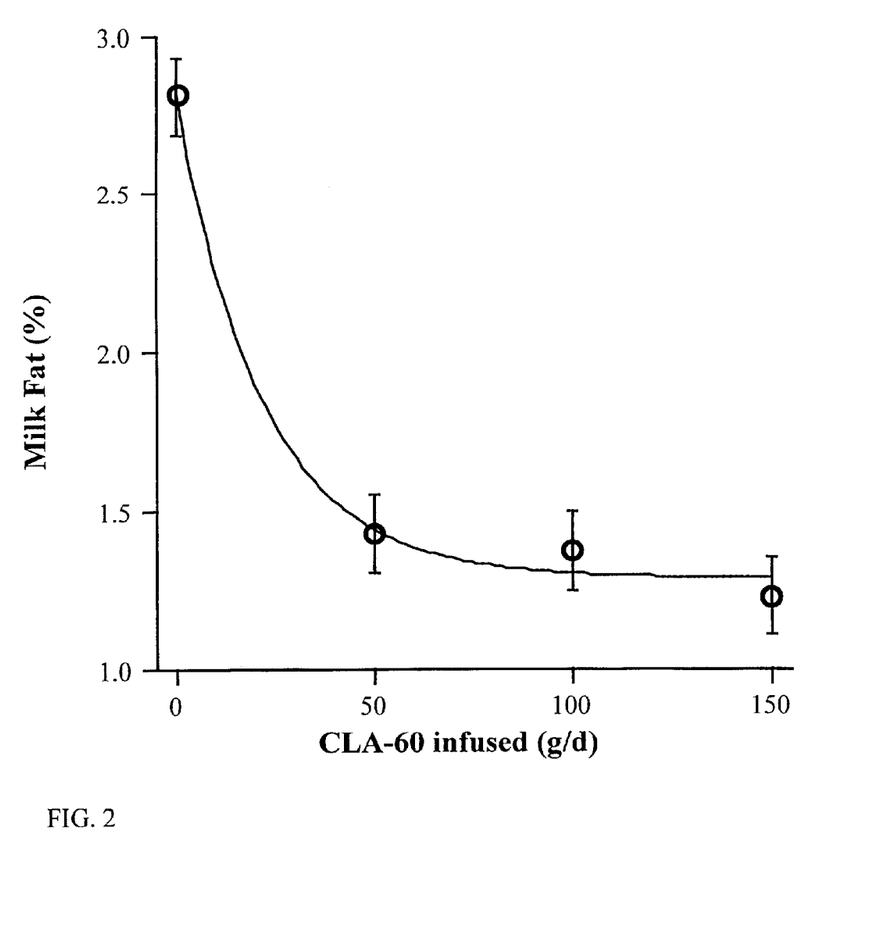
FIG. 2 shows the effect of abomasal infusion of CLA-60 on milk fat percentage.

Referring to FIG. 2, the effect of CLA on milk composition was examined by dietary addition to lactating dairy cows of a commercially available CLA product (CLA 60) which is a mixture of CLA isomers (Natural Lipids, Inc., Hovdebygda, Norway) to lactation dairy cows. CLA was delivered by infusing directly into the abomasum; this is a convenient experimental method to bypass rumen bacterial fermentation. In commercial practice the dietary supplement of CLA is coated to bypass rumen bacteria and pass directly to the abomasum. The CLA-60 mixture contained about 60% CLA with the four predominant CLA isomers being cis/trans 9,11, cis/trans 8,10, cis/trans 11,13 and cis/trans 10,12 (see Table 1).

TABLE 1

Fatty acid profile of CLA-60
(Natural Lipids LTD, Hovdebygda, Norway)

| Fatty acid | % of total fatty acids | % of total CLA |
|---|---|---|
| C16:0 | 6.4 | |
| C18:0 | 2.9 | |
| C18:1 (cis-9) | 20.8 | |
| C18:2 (cis-9, cis-12) | 3.5 | |
| *c/t 9,11 C18:2 | 14.5 | 23.7 |
| c/t 8,10 C18:2 | 9.3 | 15.2 |
| c/t 11,13 C18:2 | 10.6 | 17.3 |
| c/t 10,12 C18:2 | 21.2 | 34.5 |
| Other CLA | 5.7 | 9.3 |
| Total CLA | (61.3) | 100.0 |
| Unknown | 5.2 | |

*c/t indicates CLA has one cis and one trans double bond (e.g. cis-9, trans-11 CLA or trans-9, cis-11 CLA)
Four levels of the CLA-60 were infused (0, 50, 100 and 150 g/d) over a 5 day period in a 4 × 4 Latin square arrangement of treatments. Infusion of the CLA mixture resulted in a 50% reduction in milk fat content with MFD already maximized at the lowest dose of CLA-60 (see FIG. 2).

Figure 3:
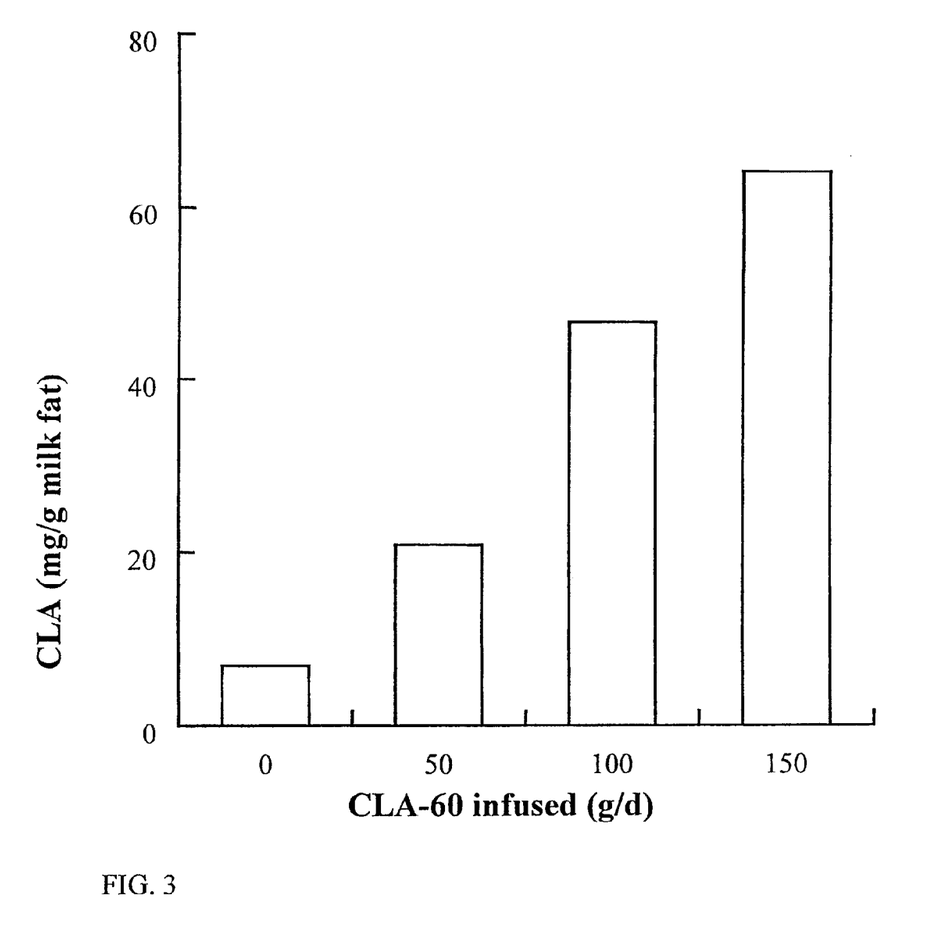
FIG. 3 shows the effect of abomasal infusion of CLA-60 on milk fat content of CLA.

Referring to FIGS. 2 and 3, CLA infusion had the effect of significantly reducing the milk fat content of milk, with no effect on milk yield except at the highest dose of CLA. In contrast to milk fat, the milk content of protein, solids not fat and ash were unchanged by CLA infusion (see Table 2).

TABLE 2

Performance during abomasal infusion of CLA-60.

| | CLA-60 infused (g,d) | | | | |
|---|---|---|---|---|---|
| | 0 | 50 | 100 | 150 | SEM |
| Dry matter intake kg/d | 22.5 | 22.0 | 21.4 | 20.2 | 1.27 |
| Milk yield kg/d | 21.5 | 20.4 | 20.9 | 18.3 | 0.84 |
| Fat | | | | | |
| % | 2.81 | 1.43 | 1.38 | 1.23 | 0.12 |
| g,d | 599 | 290 | 295 | 222 | 30.0 |
| CP | | | | | |
| % | 3.31 | 3.37 | 3.53 | 3.46 | 0.08 |
| g/d | 696 | 675 | 717 | 627 | 29.3 |

CLA infusion also markedly increased the CLA content of milk fat. The increase was dose dependent and represented a 10-fold increase over control at the 150 g/d CLA treatment (see FIG. 3). Table 2 teaches that dietary supplement with a commercially available CLA will cause a decrease in milk content of fat and an increase in milk content of CLA. The lower milk fat improves the nutritional quality of the milk for humans and results in an improved feed efficiency for the cow. Likewise, increased CLA concentration has the added advantage of provided increased levels of a compound which is a potent anticarcinogen and has numerous other health benefits.

EXAMPLE 2

Figure 4:
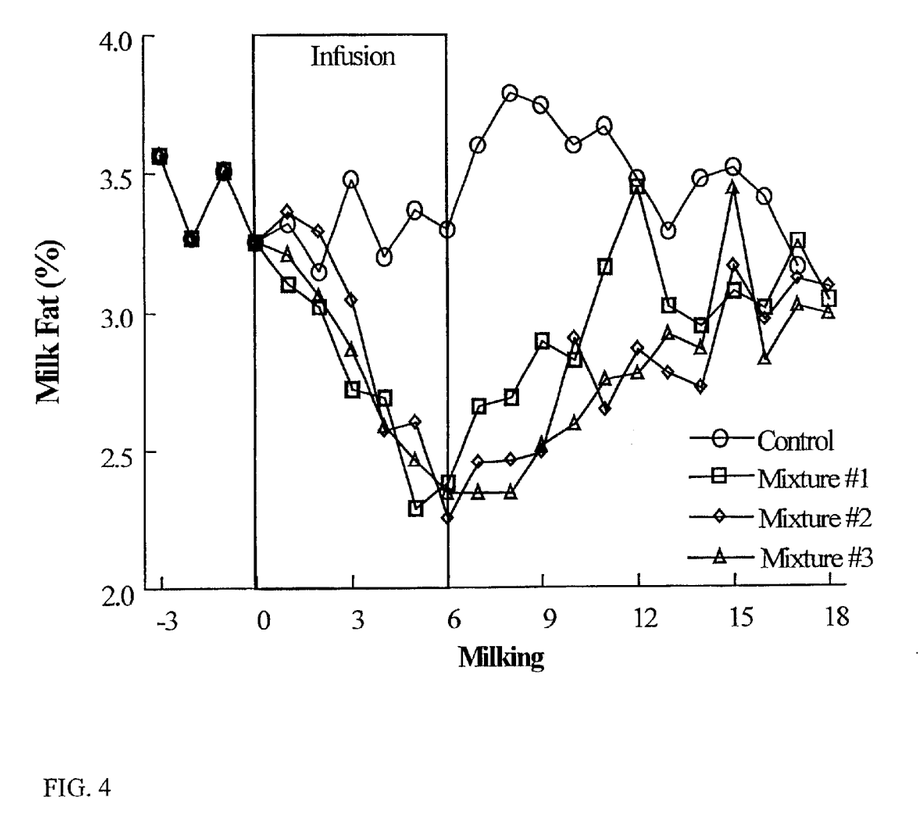
FIG. 4 shows the effect of abomasal infusion of different CLA mixtures on milk fat percentage.

CLA Enrichment: The Effect of Different Mixtures of CLA Isomers on Milk Fat Synthesis Referring to FIG. 4, three CLA enrichments were obtained (Natural Lipids Inc.) and abomasally infused over a 3-day period in a 4×4 Latin square design. The mixtures were designated #1, #2 and #3. Mixture #1 contained about 60% CLA with two major isomers, Mixture #2 contained about 60% CLA and had four major CLA isomers and Mixture #3 contained 90% CLA with two major isomers (see Table 3).

TABLE 3.

Summary of the infusion levels.

| | Treatment | | | |
|---|---|---|---|---|
| | Control | Mixture #1 | Mixture #2 | Mixture #3 |
| CLA mixture infused (g/d) | ... | 26.7 | 45.0 | 14.4 |
| Individual isomers infused (g/d) | | | | |
| c/t 9,11 C18:2 | ... | 6.2 | 6.2 | 6.2 |
| c/t 8,10 C18:2 | ... | 5.8 | 3.6 | ... |
| c/t 11,13 C18:2 | ... | 0.3 | 4.8 | ... |
| c/t 10,12 C18:2 | ... | ... | 7.3 | 6.4 |
| c/c 9,11 C18:2 | ... | 2.0 | 0.9 | 0.1 |
| c/c 10,12 C18:2 | ... | 0.2 | 0.7 | 0.1 |
| t/t 9,11 + 10, 12 C18:2 | ... | 1.3 | 1.9 | 0.1 |

The infusion of all CLA mixtures caused milk fat depression. Furthermore, the magnitude of the decrease in milk fat content was similar for all CLA mixtures (see FIG. 4). This example teaches that CLA mixtures with different enrichments of CLA isomers all cause milk fat depression.

EXAMPLE 3

Relationship Between Trans C18:1 Fatty Acids and Milk Fat Depression

The role of trans-octadecenoic acids in MFD was examined (Griinari et al. 1998). The study consisted of four experimental periods with a 2×2 factorial arrangement of treatments to test effects of dietary fats (saturated vs. unsaturated; SF vs. UF) and rumen fermentation (high fiber diet vs. low fiber diet; HF vs. LF). Effects were most pronounced when unsaturated fat was added to the low fiber diet. This treatment resulted in a 30% and 35% decrease in milk fat content and milk fat yield, respectively. In contrast milk protein was not altered (see Table 4).

TABLE 4

Effect of diet on milk fat content and yield

| | Diet* | | | | |
|---|---|---|---|---|---|
| Variable | HF/SF | HF/UF | LF/SF | LF/UF | SEM |
| Milk yield, kg/d | 29.3 | 31.7 | 26.5 | 26.3 | 1.6 |
| Milk fat | | | | | |
| % | 3.58 | 3.36 | 3.33 | 2.49 | 0.16 |
| kg/d | 1.05 | 1.06 | 0.87 | 0.68 | 0.06 |

TABLE 4-continued

Effect of diet on milk fat content and yield

| Variable | HF/SF | HF/UF | LF/SF | LF/UF | SEM |
|---|---|---|---|---|---|
| Milk protein | | | | | |
| % | 3.01 | 3.07 | 3.10 | 3.24 | 0.12 |
| kg/d | 0.87 | 0.97 | 0.82 | 0.85 | 0.03 |

Figure 5:
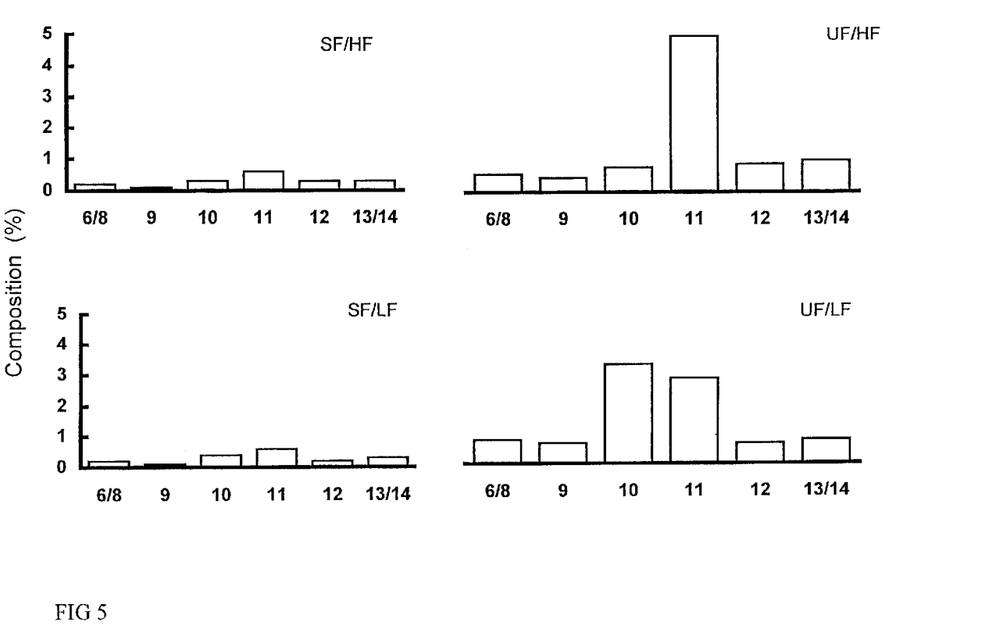
FIG. 5 shows the effect of diet on the milk fat content of trans-octadecenoic fatty acid isomers.

*HF = high fiber diet, LF = low fiber diet, SF = saturated fat supplement, and UF = unsaturated fat supplement The milk fat content of total TFA was effected by the type of fat (saturated vs. unsaturated) consistent with their origin being from incomplete bio-hydrogenation of unsaturated fat in the rumen. However, there was no relationship between total TFA and milk fat depression. Further examination of the isomeric profile of TFA in milk fat revealed major differences among dietary treatments. In particular an increase in the content of trans-10 C18:1 in milk fat was associated with the decrease in milk fat content and yield (see FIG. 5).

This example shows that the dietary induced MFD requires two conditions 1) a rumen environment and bacterial population characteristic of what occurs when low fiber diets are fed and 2) a dietary source of unsaturated fatty acids. Most important this example shows MFD is related to changes in the milk fat content of trans-10 fatty acid rather than total TFA. The origin of the trans-10 fatty acid in milk fat is incomplete bio-hydrogenation in the rumen. In addition to rumen production of trans-10, other TFA's including cis-12 CLA would be produced as well. A rumen environment similar to that caused by LF diet (low pH, high rate of passage) would also occur for the other earlier listed dietary conditions where MFD occurs.

EXAMPLE 4

CLA and Trans C18:1 Isomers Produced in the Rumen

To examine the effect of diet on the CLA and trans fatty acid isomers produced by rumen bacteria a fistula was installed in a lactating dairy cow. This allowed a comparison of fatty acid isomers produced in a lactating animal that consumed a diet resulting in normal milk fat content production and a diet which resulted in milk fat depression and a boost in CLA content. To initiate MFD a diet which included 5% sunflower oil was utilized. For each dietary period, milk fat content was monitored. Rumen fluid samples were also obtained (via the fistualated rumen) and lipids were extracted. As expected, the diet supplemented with sunflower oil caused a 44% reduction in milk fat content. Comparison of the CLA and TFA isomers showed that the MFD was related to changes in the specific pattern of isomers present in the rumen. The ratio of trans-10 fatty acid to trans-11 fatty acid was 0.3:1 for the control diet vs. 2.9:1 for the MFD diet. Likewise the ratio of trans-10, cis-12 CLA to cis-9, trans-11 CLA was 0.3:1 for the control diet vs. 3.6:1 for the MFD diet (see Table 5).

TABLE 5

Effect of MFD diet on rumen production of TFA and CLA isomers.

| | Diet | |
|---|---|---|
| Variable | Control | Sunflower oil |
| Milk fat control, % | 3.15 | 1.77 |
| Rumen fatty acids, mg/g rumen digested | | |
| Trans-10 $C_{18:1}$ | 5.98 | 13.92 |
| Trans-11 $C_{18:1}$ | 22.50 | 4.85 |
| Cis-9, trans 11 CLA | 1.13 | 0.15 |
| Trans-10, cis-12 CLA | 0.31 | 0.54 |

This example shows that dietary induced MFD corresponds to increased rumen production of trans-10 fatty acid and trans-10, cis-12 CLA. Certain rumen conditions favor bacterial colonies that in turn produce these unique fatty acids. With the presence of these unique fatty acids, and the resulting incomplete bio-hydrogenation of unsaturated fatty acids milk fat synthesis is impaired, and CLA levels are improved.

Literature Cited and Incorporated by Reference

1. Astrup, H. N., L. Vik-Mo, A. Ekern, and F. Bakke. 1976. Feeding protected and unprotected oils to dairy cows. J. Dairy Sci. 59:426–430.
2. Banks, W., J. L. Clapperton, A. K. Girdler, and W. Steele. 1984. Effect of inclusion of different forms of dietary fatty acid on the yield and composition of cow's milk. J. Dairy Res. 51:387–395.
3. Chin, S. F., J. M. Storkson, K. J. Albright, M. E. Cook and M. W. Pariza. 1994. Conjugated linoleic acid is a growth factor for rats as shown by enhanced weight gain and improved feed efficiency. J. Nutr. 124:2344–2349.
4. Davis, C. L., and R. E. Brown. 1970. Low-fat milk syndrome. Page 545 in Digestion and Metabolism in the Ruminant. A. T. Phillipson, ed. Oriel Press, Newcastle upon Tyne, England.
5. Erdman, R. 1996. Milk fat depression: some new insights. Proceedings, Tri-State Dairy Nutrition Conference, Fort Wayne, Ind., pages 1–16.
6. Gaynor, P. J., R. A. Erdman, B. B. Teter, J. Sampugna, A. V. Capuco, D. R. Waldo, and M. Hamosh. 1994. Milk fat yield and composition during abomasal infusion of cis or trans octadecenoates in Holstein Cows. J. Dairy Sci. 77:157–165.
7. Griinari, J. M., P.Y. Chouinard, and D. E. Bauman. 1997. Trans fatty acid hypothesis of milk fat depression revised. Page 208 in Cornell Nutr. Conf Feed Manuf., Rochester, N.Y. Cornell Univ., Ithaca, N.Y.
8. Griinari, J. M., D. A. Dwyer, M. A. McGuire, D. E. Bauman, D. L. Palmquist, and K. V. V. Nurmela. 1998. Trans-octadecenoic acids and milk fat depression in lactating dairy cows. J. Dairy Sci. 81:1251–1261.
9. Kalscheur, K. F., B. B. Teter, L. S. Piperova, and R. A. Erdman. 1997. Effect of dietary forage concentration and buffer addition on duodenal flow of trans-$C_{18:1}$ fatty acids and milk fat production in dairy cows. J. Dairy Sci. 80:2104–2114.
10. Newbold, J. R., K. L. Robertshaw and H. W. Morris. 1998. Associations between concentrations of fat and intermediates of ruminal biohydrogenation in milk of dairy cows. Proc. Brit. Soc. Anim. Sci., pg. 224. (abstract).
11. Pennington, J. A., and C. L. Davis. 1975. Effects of intraruminal and intra-abomasal additions of cod liver oil on milk fat production in the cow. J. Dairy Sci. 58:49–55.
12. Romo, G., D. Casper, R. Erdman, and B. B. Teter. 1996. Abomasal infusion of cis and trans fatty acid isomers and energy metabolism of lactating dairy cows. J. Dairy Sci. 79:2005–2015.
13. Selner, D. R., and L. H. Schultz. 1980. Effects of feeding oleic acid or hydrogenated vegetable oils to lactating cows. J. Dairy Sci. 63:1235–1241.
14. Teter, B. T., J. Sampugna and M. Keeney. 1990. Milk fat depression in C57B1/6J mice consuming partially hydrogenated fat. J. Nutr. 120:818–824.
15. Wonsil, B. J., J. H. Herbein, and B. A. Watkins. 1994. Dietary and ruminally derived trans-18:1 fatty acids alter bovine milk lipids. J. Nutr. 124:556–565.

The foregoing description has been directed to particular embodiments of the invention in accordance with the requirements of the Patent Statutes for the purposes of illustration and explanation. It will be apparent, however, to those skilled in this art that many modifications and changes will be possible without departure from the scope and spirit of the invention. It is intended that the following claims be interpreted to embrace all such modifications and changes.

What is claimed is:

1. A method of altering the concentration of milk fat in milk produced by a lactating mammal comprising the step of:
   administering to said lactating mammal an effective amount of a conjugated linoleic acid compound sufficient to decrease the fat content of milk produced by said lactating mammal and increase the milk content of said conjugated linoleic acid compound, such that said conjugated linoleic acid compound is capable of bypassing initial digestive processes or rumen bacterial biohydrogenation, when administered to a lactating ruminant.

2. The method of claim 1, wherein said lactating mammal is selected from the group consisting of:
   a) human;
   b) cow;
   c) goat;
   d) sheep;
   e) dog;
   f) rabbit;
   g) horse; and
   h) pig.

3. The method of claim 1, wherein said conjugated linoleic acid compound is selected from the group of conjugated linoleic acid isomers consisting of:
   a) trans-10, cis-12 conjugated linoleic acid;
   b) cis-8, trans-10 conjugated linoleic acid;
   c) trans-8, cis-10 conjugated linoleic acid;
   d) a conjugated linoleic acid compound comprising a double bond including carbon number 10; and
   e) a mixture comprising at least two of the above compounds.

4. The method of claim 1, wherein said conjugated linoleic acid compound is administered to said lactating mammal by coating said conjugated linoleic acid compound such that said conjugated linoleic acid compound is capable of bypassing initial digestive processes or rumen bacterial biohydrogenation, when administered to a lactating ruminant.

5. The method of claim 3, wherein said lactating mammal is a cow.

6. The method of claim 3, wherein said conjugated linoleic acid compound is administered to said lactating mammal by coating said conjugated linoleic acid compound such that said conjugated linoleic acid compound bypasses initial digestive processes or rumen bacterial biohydrogenation and passes directly to the abomasum, when administered to a lactating ruminant.

7. A method of altering the concentration of milk fat in milk produced by a lactating mammal comprising the step of:
   administering to said lactating mammal an effective amount of a conjugated fatty acid compound sufficient to decrease the fat content of milk produced by said lactating mammal and increase the milk content of said conjugated fatty acid compound, such that said conjugated fatty acid compound is capable of bypassing initial digestive processes or rumen bacterial biohydrogenation, when administered to a lactating ruminant.

8. The method of claim 7, wherein said lactating mammal is selected from the group consisting of:
   a) human;
   b) cow;
   c) goat;
   d) sheep;
   e) dog;
   f) rabbit;
   g) horse; and
   h) pig.

9. The method of claim 7, wherein said conjugated fatty acid compound is selected from the group consisting of:
   a) trans-10, cis-12 conjugated linoleic acid;
   b) cis-8, trans-10 conjugated linoleic acid;
   c) trans-8, cis-10 conjugated linoleic acid;
   d) a conjugated fatty acid compound comprising a double bond including carbon number 10;
   e) a conjugated octadecenoic fatty acid compound having at least two double bonds; and
   f) a mixture comprising at least two of the above compounds.

10. The method of claim 7, wherein said conjugated fatty acid compound is administered to said lactating mammal by coating said conjugated fatty acid compound such that said conjugated fatty acid compound is capable of bypassing initial digestive processes or rumen bacterial biohydrogenation, when administered to a lactating ruminant.

11. The method of claim 7, wherein said lactating mammal is a cow.

12. The method of claim 7, wherein said conjugated fatty acid compound is coated, such that said conjugated fatty acid compound bypasses initial digestive processes or rumen bacterial biohydrogenation and passes directly to the abomasum, when administered to a lactating ruminant.

* * * * *